US005631243A

United States Patent [19]
Kelman et al.

[11] Patent Number: 5,631,243
[45] Date of Patent: May 20, 1997

[54] COLLAGEN-BASED VISCOELASTIC SOLUTION FOR VISCO-SURGERY

[75] Inventors: Charles D. Kelman, New York, N.Y.; Dale P. DeVore, Chelmsford, Mass.

[73] Assignee: Collagenesis Inc., Acton, Mass.

[21] Appl. No.: 365,167

[22] Filed: Dec. 28, 1994

Related U.S. Application Data

[63] Continuation of Ser. No. 939,955, Sep. 3, 1992, abandoned, which is a continuation of Ser. No. 547,458, Jul. 3, 1990, abandoned.

[51] Int. Cl.⁶ .................... A61K 31/725; A61K 31/715; A61M 31/00
[52] U.S. Cl. .................... 514/56; 514/54; 514/62; 514/912; 514/801; 514/2; 514/21; 424/427; 604/51
[58] Field of Search .................... 514/56, 54, 2, 514/21, 62, 912, 801; 536/4.1, 123, 119, 55.1; 530/356; 623/4; 424/427; 128/DIG. 8; 604/48, 51

[56] References Cited

U.S. PATENT DOCUMENTS

| | | | |
|---|---|---|---|
| Re. 32,969 | 6/1989 | Trager et al. | 514/912 |
| 2,827,419 | 3/1958 | Tourtellott et al. | 514/801 |
| 3,034,852 | 5/1962 | Nishihara | 435/68.1 |
| 3,314,861 | 4/1967 | Fujii et al. | 435/68.1 |
| 4,141,973 | 2/1979 | Balazs | 536/4.1 |
| 4,328,803 | 5/1982 | Pape | 514/54 |
| 4,418,691 | 12/1983 | Yannas et al. | 623/15 |
| 4,581,030 | 4/1986 | Bruns et al. | 623/4 |
| 4,582,865 | 4/1986 | Balazs et al. | 524/29 |
| 4,663,166 | 5/1987 | Veech | 514/23 |
| 4,705,682 | 11/1987 | Moeller et al. | 252/356 |
| 4,713,446 | 12/1987 | DeVore et al. | 514/801 |
| 4,748,152 | 5/1988 | Miyata et al. | 424/427 |
| 4,819,617 | 4/1989 | Goldberg et al. | 536/98 |
| 4,851,513 | 7/1989 | DeVore et al. | 514/801 |
| 4,882,284 | 11/1989 | Kirchanski et al. | 436/172 |
| 4,883,864 | 11/1989 | Scholz | 514/21 |
| 4,929,242 | 5/1990 | Desecki et al. | 604/266 |

OTHER PUBLICATIONS

Dijke et al., Biotechnology, vol. 7, Aug. 1989, pp. 793–798.
K.H. Stenzel et al. (1967), "Collagen–Derived Membrane: Corneal Implantation", *Science*, vol. 157, pp. 1329–1330.
K.H. Stenzel et al. (1969), "Collagen Gels: Design for a Viteous Replacement", *Science*, vol. 164, pp. 1282–1283.
A.L. Rubin et al. (1965), "Effects of Pepsin Treatment on the Interaction Properties of Tropocollagen Macromolecules", *Biochemistry*, vol. 4 (2), pp. 181–189.
Devore Dale P. et al., Rheology of Sodium Hyaluronate Solutions and Relevance to Their Use as Medical Implants, Mat. Res. Soc. Proc. vol. 110, pp. 455–461.
Arshinoff S.A., Viscoelastic Substances: Their Properties and Use When Placing An Iol in the Capsular Bag, Curr. Can. Ophthalmic Prac. 4:2, 64–65 and 72–74, 1986.
MacRae et al., The Effects of Sodium Hyaluronate, Chondroitin Sulfate and Methylcellulose on the Corneal Endothelium and Intracular Pressure, Amer. J. Ophthal. 95:332–341, 1983.
Balasz, E., Sodium Hyaluronate and Viscosurgery, Healon, Miller, D. and Stegman, R., eds. John Wiley & Sons, New York, 1983, pp. 5–28.
Lutjen–Drecoll, E., ARVO Annual Meeting Abstracts, Apr. 29–May 4, 1990, Association for Research in Vision and Ophthalmology, vol. 31(4), p. 184.
Dijke et al., Bio/Technology, 7:793–798, 1989.
The Methodology of Connective Tissue Research, D. Hall, ed., Joynson–Bruvvers, Ltd., Oxford, p. 227.
Bitter & Muir, Anal. Biochem., 4:330, 1962.

*Primary Examiner*—Michael G. Wityshyn
*Assistant Examiner*—Francisco C. Prats
*Attorney, Agent, or Firm*—Darby & Darby

[57] ABSTRACT

The present invention relates to a method of treating a patient with visco-surgery, particularly ocular visco-surgery, utilizing a collagen-based viscoelastic solution having a reversibly high viscosity. The invention also relates to collagen-based viscoelastic solutions which further include mucopolysaccarides or growth factors.

23 Claims, No Drawings

COLLAGEN-BASED VISCOELASTIC SOLUTION FOR VISCO-SURGERY

This is a continuation, of Ser. No. 07/939,955, filed Sep. 3, 1992, now abandoned, which is a continuation of application Ser. No. 07/547,458, filed Jul. 3, 1990, now abandoned.

FIELD OF THE INVENTION

The present invention relates to viscoelastic solutions of collagen suitable for use in visco-surgery, particularly ophthalmic visco-surgery. Specifically, the present invention relates to such viscoelastic solutions wherein their viscosity is dramatically reduced upon the addition of solutions containing cations, such as saline solution, balanced salt solution, etc.

BACKGROUND OF THE INVENTION

Aqueous lubrication solutions have widespread use in ophthalmic surgery as protective agents for the easily damaged intraocular tissues. A major concern in ophthalmic surgery has been the frequent observation of elevated intraocular pressure associated with the surgical use of viscoelastic solutions. Elevated intraocular pressure can reduce the flow of blood-born oxygen and nutrients to the eye and to the optic nerve. Not surprisingly, such elevated pressure is strongly correlated with loss of vision (glaucoma). It is, thus, desirable that solutions for ophthalmic surgery be easily removed from eye tissues by irrigation and aspiration. It is further desirable that any residues remaining in the eye show reduced tendency to induce elevated ocular pressure.

A number of solutions have been used or proposed for use as viscoelastic solutions These include solutions of sodium hyaluronate (Healon ™, Phamacia LKB Biotechnology, Inc. and Amvisc™, IOLAB); chondroitin sulfate; mixtures with chondroitin sulfate with sodium hyaluronate (Viscoat™, Cooper-vision/ALCON); methylcellulose; carboxymethylcellulose; polyacrylamide or polymethacrylamide; and collagen derivatives. A number of these solution are reviewed by Arshinoff, *Curr. Can. Ophthalmic Prac.* 4:64–74, 1986.

Sodium hyaluronate solutions are the most widely used viscoelastic solutions for ophthalmic surgery Balazs (U.S. Pat. No. 4,141,973) or Pape (U.S. Pat. No. 4,328,803) describe their manufacture and/or use. These solutions, however, have been found to induce transient elevations in intraocular pressure. They have the further disadvantage of being expensive and failing to adhere to ocular prostheses and surgical instruments.

Chondroitin sulfate solutions are not pseudoplastic (and not viscoelastic) and consequently are difficult to inject through the narrow gauge needles used in ophthalmic surgery (see MacRae et al., "The Effects of Sodium Hyaluronate, Chondroitin Sulfate and Methyl Cellulose on the Corneal Endothelium and Intraocular Pressure," *Amer. J. Ophthal.* 95:332–341, 1983). Additionally, these solutions are less effective than sodium hyaluronate solutions in maintaining space between separated ocular tissues Finally, such solutions are associated with sharp elevations in intraocular pressure.

Unmodified collagen is usually unsuitable for ophthalmic solutions due to its low solubility at pH values close to neutral pH. However, Devore et al. (U.S. Pat. Nos. 4,713,446 and 4,851,513) and Miyata et al. (U.S. Pat. No. 4,748,152) have developed collagen-based viscoelastic solutions wherein the collagen is derivatized at lysyl amino acids to increase its solubility at neutral pH.

Miyata et al. (supra) teach partially succinylated ateleopeptide collagen dissolved in physiologic saline. The viscosities taught therein are modest (highest is 10,000 centipoise for a 3% solution). Miyata et al. have no teachings relating to a collagen solution that is readily irrigated out of eye tissues. Nor are there any disclosures in Miyata et al. of the effects of the solution on intraocular pressure.

Devore et al. (supra) teach a method of producing collagen suitable for viscoelastic solutions by acylating the lysyl amino acids of collagen with a combination of monofunctional and bifunctional reagents. The result of this acylation treatment is that some collagen lysine amino groups are modified to substitute a carboxylic acid group in place of the basic amino function. The residue of the lysine amino groups are covalently linked to lysine amino groups of the same or an adjacent collagen molecule. The viscoelastic solution is produced by reconstituting this derivatized collagen in a physiologic saline solution. These are no disclosures in the Devore et al. patents of collagen viscoelastic solutions that are readily irrigated out of ocular cavities. Neither is there any disclosure of the effects of the collagen solutions taught therein on intraocular pressure.

Desirable properties of viscoelastic solutions include: transparency; stability (i.e. they maintain their useful properties over long term storage); high viscosity; pseudoplasticity; viscoelasticity; thixotropy; and biological compatibility.

Pseudoplastic solutions are useful in visco-surgery because their viscosity drops when they are subjected to high shear flow, such as occurs during injection through the high gauge (narrow) needles used in ophthalmic surgery. (Pseudoplastic fluids are non-Newtonian fluids wherein the kinetic viscosity (centipoise-sec or cps) decreases as the sheer rate increases.) Thus, pseudoplastic surgical solutions are injectable despite their viscosity.

Viscous solutions are useful due to their tendency to resist flowing out of the ocular cavity into which they have been injected.

Viscoelastic solutions are useful in viscosurgery because they resist having their shape deformed (i.e., they are elastic), thus helping to maintain the shape of body cavities into which the solutions are injected. (The elasticity of the solution results in the Weissenberg Effect, which describes the tendency of viscoelastic solutions to flow at right angles to an applied force.) During surgery, viscoelastic materials protect cell and tissue surfaces from mechanical trauma; create space by separating two adjacent but not adherent tissue surfaces, or by breaking normal or pathological tissue adhesions; maintain space, for instance, in the interior chambers of the eye or in the lens sack, allowing for safe surgical manipulations by permitting the insertion of implants without dislocating or touching sensitive tissues; contain hemorrhages; and also act as a "soft instrument" or "surgical tool" to move, manipulate or relocate tissues.

Following injection of a viscoelastic solution, at high shear, through a narrow gauge needle (e.g. into a chamber of the eye), it is useful for the solution to regain the majority of its viscosity. Solutions having this recovery property are "thixotropic."

A biocompatible substance, as used herein, shall be noninflammatory, nontoxic, nonimmunogenic, pH buffered and shall have osmolarity between about 200 milliosmoles and about 400 milliosmoles, preferably between about 250 milliosmoles and about 350 milliosmoles, most preferably between about 280 milliosmoles and about 330 milliosmoles.

What is needed in the art is a viscoelastic solution that has transparency, stability, high viscosity, pseudoplasticity, viscoelasticity, thixotropy, and biological compatibility, but moreover, can be used in ophthalmic surgery with reduced risk of elevated intraocular pressure.

BRIEF DESCRIPTION OF THE INVENTION

The present inventors have unexpectedly discovered that soluble collagen, when reconstituted in low ionic strength buffers, shows markedly increased viscosity and continues to have viscoelastic properties. This increased viscosity is maintained as the osmolarity of the solution is increased using nonionic solutes.

By this invention, high viscosity solutions useful for ophthalmic surgery (or any visco-surgery involving delicate tissue in need of protection) can be prepared at lower collagen concentrations. The viscosity of the solution can, subsequently, be dramatically lowered by simply diluting or irrigating with saline solutions. Thus, the viscoelastic solutions of the present invention are easily irrigated out of ocular cavities following ophthalmic surgery. Therefore, their use reduces the risk of elevated intraocular pressure associated with residues of viscoelastic solution remaining in the eye following surgery.

It has been discovered that viscoelastic solutions according to the present invention reduce the risk of elevated ocular pressure even when they are not washed out of ocular spaces.

The addition of mucopolysaccoharides, such as chondroitin sulfate, and growth factors, such as epidermal growth factor (EGF) or growth hormone (GH), to the viscoelastic solutions used in the present invention is expected to provide further benefits.

DETAILED DESCRIPTION OF THE INVENTION

The viscoelastic collagen solutions of the present invention have osmolarities ranging between about 260 and 340 milliosmoles, about 75% to about 95% of the osmolarity provided by nonionic solutes such as glycerol.

Such solutions have been found to have higher viscosities or the same viscosity at lower concentrations of soluble collagen then comparable collagen solutions dissolved in physiologic saline solutions. Collagen suitable for use in the present invention can be prepared by reacting collagen (at its lysyl amino acids) with an acylating agent, e.g., glutaric anhydride, succinic anhydride, heptafluorobutyric anhydride, methacrylic anhydride, phthalic anhydride, methyl glutaric anhydride, dimethyl glutaric anhydride, benzene sulfonic acid, β-styrene sulfonyl chloride, hydroquinone sulfonic acid, polyvinyl sulfonic acid, etc. For instance:

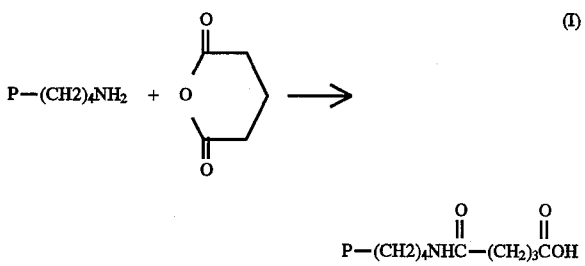

where P is the collagen backbone. The above reaction reverses the ionic charge at physiologic pH of the reacted lysyl amino acids (plus to minus). The reaction also increases the solubility at physiologic pH of the collagen product.

Such collagen can be reconstituted (following intermediate processing steps) in sodium phosphate buffer to give a kinetic viscosity of 30,000 cps (at $1$ $sec^{-1}$) and dialyzed against distilled water. After 24 to 72 hours of dialysis, the viscosity is dramatically increased (e.g. 200,000 cps). The viscosity of the solution can be reduced to about 60,000 cps by dilution with distilled water. The osmolarity of such a solution of collagen can be increased to the physiologic range (205 to 405 milliosmoles) by addition of a nonionic solute, such as glycerol, without substantial loss of viscosity. However, the addition of salt to increase the ionic strength to at least $0.0022\mu$ produces a drop in viscosity of as much as 88% (with dilution effects accounting for none of the viscosity drop). Preferably, the addition of salt to increase the ionic to $0.0043\mu$ produces a drop in viscosity of at least 50 fold. The dialysis step is not essential to the invention. Comparable high, reversible viscosities are seen with collagen solutions that are reconstituted simply by dissolving precipitated or lyophilized collagen in low saline buffer.

It is known in the prior art that dialysis of collagen against water results in long strands of end-to-end associate collagen molecules (see Bruns et al., U.S. Pat. No. 4,581,030). Such end-to-end association results in increased effective molecular weight and some associated increase in viscosity. While not wanting to be restricted to theory, this previously observed phenomenon does not adequately explain the dramatic viscosity effects described herein. The dramatic increase in viscosity seen in the solutions of the present invention (e.g., 30,000 cps increased to 200,000 cps) suggest more complex, multiple interactions such as seen for hyaluronate solutions (see Balasz, E., Sodium Hyaluronate and Viscosurgery, Healon, Miller, D. and Stegman, R., eds. John Wiley & Sons, New York, 1983).

The viscoelastic collagen solutions of the present invention are prepared by reconstitution of collagen in a low saline physiologic buffer. "Reconstitution," as used herein, means any method of obtaining collagen dissolved in a desired buffer. This may be done by a number of methods including:

1) Dialysis to exchange the buffer dissolving collagen for the desired buffer.
2) Redissolving precipitated collagen in the desired buffer.
3) Dilution of a collagen solution with a buffer concentrate to obtain the desired buffer composition.

As used herein, "low saline" buffer shall mean buffer having ionic solutes that yield no more than about $0.001\mu$ of the ionic strength, preferably no more than about $0.0008\mu$. A "low saline physiologic" buffer shall meet the above saline requirement and have nonionic solutes for a total osmolarity between about 200 and about 400 milliosmoles, preferably between about 250 and about 350 milliosmoles, most preferably between about 280 and about 330 milliosmoles.

Appropriate nonionic solutes include glycerol, sorbitol, xylitol, threitol, mannitol, arabitol, ribitol, adonitol, erythritol, dulcitol, altritol, iditol, various heptoses, hexoses and pentoses, polyglycols, etc.

Since mucopolysaccarides such as chondriotin sulfates (e.g., chondroitin sulfate A, B or C) adhere to endothelial cells, it is anticipated that the addition of mucopolysaccarides to the viscoelastic collagen solutions will also increase the adherence of the solution. This increase in adherence should enhance the protection of endothelial tissues (such as the tissues lining the ocular cavities). While the source of the affinity of such mucopolysaccharides for endothelial cells is not completely understood, it may, in part, be due to the receptors for mucopolysaccharides which are present on the endothelium (Lutjen-Drecoll, E., *ARVO Annual Meeting Abstacts*, Apr. 29–May 4, 1990, Association for Research in Vision and Opthamology, publisher, Vol. 31(4), p. 184). Other mucopolysaccarides which should be useful adherence promoting additives to the viscoelastic collagen solutions are salts of hyaluronic acid, dermatan sulfate (also known as chondroitin sulfate B), keratan sulfate, heparan sulfate, etc. A useful range of collagen to mucopolysaccaride weight ratios is anticipated to be between about 100:1 and about 10:1, more preferably between about 40:1 and about 20:1.

Hyaluronic acid is available from Sigma Chemical Co., St. Louis, MO (from human umbilical cord, bovine vitreous and rooster comb) and from Calbiochem Biochemicals, San Francisco, Calif. (from human umbilical cord). Chondroitin sulfate A is available from Sigma Chemical Co. (from bovine trachea) and Calbiochem (from bovine trachea). Chondroitin sulfate B is available from Sigma Chemical Co. (from bovine mucosa, porcine skin) and Calbiochem (from porcine mucosa). Chondroitin sulfate C is available from Sigma Chemical Co. (from shark cartilage) and Calbiochem (from shark cartilage). Keratan sulfate is available from Sigma Chemical Co. (from bovine cornea) as is heparan sulfate (from bovine intestinal mucosa and bovine kidney). A number of these mucopolysaccharides are also available from Seikagaku Kogoyo Co., Ltd., Tokyo, Japan.

Growth factors (such as EGF, transforming growth factors (TGFs) GH, interleukins, fibroblast growth factors (FGFs), platelet-derived growth factors (PDGFs), insulin-like growth factors (IGFs), etc.) may be added to the collagen viscoelastic solution. These growth factors are anticipated to enhance the viability of the tissues manipulated and exposed during the course of visco-surgery. The amount of growth factor added to the viscoelastic solution of the present invention will vary with the specific growth factor, but will generally be in the range of 10–1,000 ng/ml. The range for EGF is anticipated to be between about 1 ng/ml and about 100,000 ng/ml; for FGFs between about 10 ng/ml and about 500 ng/ml; and for PDGFs and IGFs between about 10 ng/ml and 10,000 ng/ml.

Growth factors have been found to enhance the rate of wound healing in many tissues, including corneal tissues (see Dijke et al., *Bio/Technology*, 7:793–798, 1989). Accordingly, it is anticipated that growth factors will enhance the rate of recovery of corneal tissue from the trauma of viscosurgery. For example, EGF has been shown to increase corneal reepithelialization and to stimulate corneal cell-proliferation and migration. In addition, preliminary data suggests that EGF enhances corneal reinnervation and stimulates into corneal endothelial cell-proliferation.

EGF is available from Amgen, Thousand Oaks, CA and Sigma Chemical Co.; fibroblast growth factors are available from Amgen Biochemicals and R&D Systems, Oxford, England; transforming growth factors are available from R&D Systems; and PGFs are available from R&D Systems and Collaborative Research, Inc., Medford, Mass. Interleukins are available from R&D Systems and Collaborative Research, Inc.; IGFs are available from R&D Systems; and GH is available from Cambridge Medical Technologies Corp., Billerica, Mass. and Boehringer Mannheim Corp., Indianapolis, Ind.

The pH of the viscoelastic collagen solution is preferably stabilized generally by between about 5 mM and about 50 mM of buffer. Buffers that are usable with the invention are any that are biologically compatible. These include phosphate buffers, carbonate buffers, and phosphate-bicarbonate.

The saline solutions that may be used to reduce the viscosity of the viscoelastic solutions of the present invention include any of the numerous such solutions that are used in medicine or biology research for non-disruptive manipulation of tissues and cells. These include numerous phosphate buffered saline solutions (e.g., 0.84 percent by weight NaCl, 0.054 by weight KCl, 0.028 percent by weight $Na_2HPO_4$, 0.004 percent by weight $NaH_2PO_4$, and, optionally, 0.017 percent by weight $CaCl_2$), Hank's balanced salt solutions (GIBCO Labs., Grand Island, New York) and Balanced Salt Solutions available from several ophthalmic pharmaceutical companies, including Alcon Laboratories (Ft. Worth, Tex.), Pharmafair (Hauppauge, N.Y.), Akorn, Inc. (Abita Springs, La.), and Allergan Pharmaceuticals (Irvine, Calif.). In general, these saline solutions will have osmolarities ranging from about 280 to about 340 milliosmoles and sodium salts in excess of potassium salts (e.g., 20.5 to 1 ratio such as for the above-described phosphate buffered saline solution).

Collagen suitable for use in the present invention is soluble at physiologic pH. Usually, this means a collagen that has been reacted with an acylating agent having two or more carboxylic acids or carboxylic acid derivatives. The degree of reaction being effective to substantially solubilize collagen at physiolic pH. For Type I collagen an effective degree of acylation is thought to be in excess of 35% of collagen lysyl amino acids acylated. Type IV collagen, when isolated from the placenta, is soluble a physiologic pH without further processing. Type II and Type III collagen are not as abundant as Type and Type IV and are for this reason alone, no anticipated to have as much utility in the practice of the present invention as Types I and IV. However, these collagens are anticipated to be solubilized by substantially the same degree of acylation as is effective for Type I collagen.

It is anticipated that collagen from unusual sources or tissues not traditionally used as a source of commercial collagen may have somewhat different solubility properties. The degree of acylation required to prepare such collagen for use in viscoelastic solutions with the viscosity properties of the present invention can be determined by routine experimentation. Such viscoelastic solutions are within the scope of the present invention.

A preferred acylating reaction for the solubilization of collagen is taught in U.S. Pat. Nos. 4,851,513 and 4,713,446. Also preferred is acylation using glutaric anhydride (reaction pH between about 7.0 and about 9.0). Another source of collagen suitable for use in the present invention is disclosed in U.S. patent application Ser. No. 157,638, filed Feb. 18, 1988now U.S. Pat. No. 4,969,912, wherein a method is taught for solubilizing telopeptide-containing collagen from comminuted animal tissue using acylating reagents. (All patents, patent publications and literature citations found herein are incorporated by reference into this disclosure.)

The acylating reagents useful for preparing the collagen used in the present invention include $C_3$ to $C_8$ organic compounds having two or more carboxylic acid-related functional groups, at least one of which is an amino-reactive form (e.g., acid halide, acid anhydride, ester, alkyl cyanate).

Usually, the collagen will be prepared from a nonhuman crude collagen source. The method for obtaining the collagen from the crude collagen source, e.g., tendon, hide, etc., is normally not critical, and some flexibility may be used in the selection of the particular tissue and the method applied thereto. Applicants prefer to extract collagen from a connective tissue, such as bovine hide. If the collagen is to be used for ophthalmic applications, it is preferred that it be obtained solely from the corium layer of the bovine hide, otherwise known as "split" hides. Split hides are commercially available from the Andre Manufacturing Co., Newark, N.J.

The collagen may be solubilized by any of the standard extraction methods, e.g., acid or salt extraction, enzymedigestion, or a combination of these. The acylation-dependent solubilization of U.S. patent application Ser. No. 157,638 (supra) may also be used. Preferably, dehaired and cleaned hide is solubilized with a proteolytic enzyme (pepsin, for example) and solubilized collagen is precipitated at pH 7, after inactivation and removal of the enzyme, by addition of NaCl to about 2.5M. Pepsin-treated collagen precipitates leaving behind in solution (to be discarded) the digested nonhelical terminal peptides of the collagen molecule and other non-collagenous contaminates, e.g., saccharides, mucopolysaccharides, etc. Inactivated enzymes are removed by filtration and centrifugation at 4° C. The pepsin-treated collagen is then further purified by repeated redissolution in acidic water (pH 2–4) and reprecipitation by salt treatment, e.g., by the addition of 0.8M sodium chloride solution at pH 3.

It is preferred that the chemicals used during collagen processing, particularly the final stages of processing, be free of inflammatory contaminants (e.g., pyrogens).

It is preferred that the kinetic viscosity of the viscoelastic solutions of the present invention be at least about 1,000 cps, but less than about 500,000 cps. It is particularly preferred that the viscosity be between about 45,000 cps and about 80,000 cps. It is preferred that upon addition of at least equal volumes of irrigating solution, such as Balanced Salt Solution, the kinetic viscosity should drop at least 50%. It is particularly preferred that this drop in viscosity be at least 75%.

The invention is described below with specific working examples which are intended to illustrate the invention without limiting the scope thereof.

EXAMPLE 1

One liter of sterile filtered, purified, atelopeptide collagen (1.5 mg/ml to 4.0 mg/ml) in 0.1M acetic acid is placed in a pyrogen-burnt glass beaker and stirred with a magnetic stir bar. A sterile solution of 10N NaOH is added to bring the pH to about 9.0. Sterile glutaric anhydride (18% by weight of the collagen weight) is added to the solution as a powder. Through the course of the acylation procedure the pH is maintained at about 9.0 by incrementally adding sterile 1N NaOH. After approximately 2 minutes, succinic dichloride is added (7% by weight of the collagen weight) via a syringe outfitted with an 0.2 µm Gelman syringe filter (Gelman Sciences Inc., Ann Arbor, Mich.). After 30 minutes, another portion of glutaric anhydride (18% by weight of collagen weight) is added. After an additional 60 minutes, the acylation is stopped by addition of 6N HCl until the pH is 4.3. Under these conditions, the acylated collagen precipitates.

After 60 minutes, the collagen precipitate is collected by centrifugation. The precipitate is washed three times by resuspension in pyrogen-free water and centrifugation. The collagen is then resuspended in approximately 80 ml of 0.005M sodium phosphate buffer the osmolarity adjusted to 305±25 milliosmoles with glycerol (pH 7.4±0.4). After an overnight incubation, the collagen is completely dissolved. The solution is then diluted by small increments until the viscosity (measured from aliquots using a Brookfield Viscometer, Brookfield Instruments, Stoughton, Mass.) is between about 45,000 cps and about 80,000 cps at a shear rate of 1 sec$^{-1}$. The osmolarity and pH of the sampled alloquots are also monitored. The osmolarity is monitored using a Precision Micro Osmometer (Precision Systems, Natick, Mass.) and adjusted by dilution with glycerol-free sodium phosphate buffer (0.005M) or by addition of glycerol. The pH is monitored with a pH electrode (Orion Research, Cambridge, Mass.) and adjusted with NaOH or HCl solutions as appropriate.

The concentration of collagen is then measured based on hydroxyproline content determined using the method of Woessner (In *The Methodology of Connective Tissue Research*, D. Hall, ed., Joynson-Bruvvers, Ltd., Oxford, page 227). Uronic acid content, an indicator of glycosaminoglycan presence, is measured using the standard carbazole method (Bitter & Muir, *Anal. Biochem.*, 4, page 330, 1962). As a further quality control measure, a UV scan is performed on each lot of collagen-based viscoelastic solution.

Once the viscosity, osmolarity and pH are adjusted to the specification values (see Table I), the solution is filtered through a sterile 5.0 µm filter.

TABLE I

| Viscoelastic Collagen Solution Specifications | | |
|---|---|---|
| Characteristic | Acceptable | Preferred |
| Osmolarity | 305 ± 100 m Osmol | 305 ± 25 m Osmol |
| pH | 7.4 ± 0.6 | 7.4 ± 0.4 |
| Color | — | Colorless |
| Viscosity | 1,000–500,000 cps[a] | 45,000–80,000 cps |
| Endotoxin | <500 Eu/ml[b] | <5 Eu/ml |
| Collagen Concentration | <10% (w/v) | <2.0% (w/v) |
| Melt Temperature | 5–100° C. | 30–40° C. |
| Sterility | Sterile | Sterile |
| Ionic Strength | ≦0.001µ | ≦0.0008µ |

[a]At a shear rate of 1 sec$^{-2}$.
[b]Eu = endotoxin units.

EXAMPLE 2

Lot A and comparative Lot A' collagen solutions were acylated as outlined in EXAMPLE 1, but were redissolved after the washing step as follows:

Lot A:
  Collagen was redissolved in 0.1N sodium phosphate, pH 7.69, with glycerol added to adjust the osmolarity to 326 milliosmoles.
  Viscosity was 69,200 cps (at 1 sec$^{-1}$) at a collagen concentration of 1.13% (w/v).

Lot A':
  Collagen was redissolved in 1N sodium phosphate buffer, pH 7.0, with the final osmolarity adjusted by dilution with sterile water to 268 milliosmoles.
  Viscosity was 43,800 cps (at 1 sec$^{-1}$) at a collagen concentration of 3.9% (w/v).

EXAMPLE 3

Two more lots (B and C) were prepared by acylating atelopeptide collagen with glutaric anhydride alone. These lots were redissolved, following three water wash steps (comparable to those outlined in EXAMPLE 1), in 1N sodium phosphate buffer. These lots were then dialyzed against deionized water for two days. Lot B was adjusted to a protein concentration of 1.55% (w/v), a pH of 6.8, and a osmolarity (adjusted with glycerol) of 275 milliosmoles. The kinetic viscosity was 228,000 cps (at 1 sec$^{-1}$).

FIG. 1 shows the kinetic viscosity profile (log (shear rate) vs. log (poise.sec)) for Lot C before (open symbols) and after dialysis (closed symbols). The collagen concentration was 1.4% (w/v) and the pH was 6.8. Notice the dramatic increase in viscosity obtained after dialysis.

EXAMPLE 4

Adult female, New Zealand white rabbits (5–6 lbs.) were used for an ocular vitreous replacement study. One day prior to the study, by slit lamp evaluation both eyes of each animal were examined using fluorescein dye to determine the condition of corneal epithelium. The corneal epithelium was evaluated to determine if any corneal abrasion, ulceration or irregularities were present. On the day of the study, each animal was again evaluated prior to the injection of the test material. Fluorescein dye was not used in this pre-injection evaluation. Animals exhibiting pre-existing corneal, lens or conjunctival injury, irritation or irregularity were not used in this study.

General anesthesia was achieved by intramuscular injection of Rompun (10 mg/kg body weight) and Ketamine HCl (50 mg/kg body weight). The pupil was dilated with 0.05 ml of 1% Cyclopentolate HCl and 2.5% Phenylephrine HCl administered topically. One drop of Proparacaine 0.5% was administered topically prior to injection of the vitreous replacement solution. All injected solutions were sterile and administered undiluted. The effects on intraocular pressure of Lot A and Lot A' (Example 2), Viscoat™ and Healon™ were compared. Viscoat™ was purchased from Alcon-Cooper/Cilco. Healon™ was purchased from Pharmacia (Uppsula, Sweden). All viscoelastic solutions were refrigerated at 6° C. until the time of use.

One rabbit eye was prepared for surgery and a 25-gauge butterfly infusion needle was inserted at the 10 o'clock position, 0.2 mm anterior to the limbus. To prevent collapse of the anterior chamber, the outflow tubing remained capped until the injection of the viscoelastic solution was initiated. A 1 cc syringe with a 27 gauge needle was filled with the viscoelastic solution to be injected into the eye to replace the vitreous and inserted at the 2 o'clock position, 0.2 mm anterior to the limbus. The beveled edges of the needles were positioned away from the corneal endothelium. The anterior chamber of the eye was filled with 0.15 cc of the viscoelastic solution. After replacement of the aqueous humor with the test material, the outflow and the inflow needles were removed. In the other eye, no viscoelastic solution was injected into the anterior chamber. This eye served as a baseline for intraocular pressure measurements. The intraocular pressure was monitored with a pneumotonometer. Eyes were evaluated prior to injection and at 0, 1, 3, 5, 24 and 48 hours post-injection.

The results obtained, using three rabbits for each measurement, are shown in TABLES II and III.

TABLE II

| | Intraocular Pressure/mm Hg | | | | | |
|---|---|---|---|---|---|---|
| | Pre-Injection | 1 hour | 3 hours | 5 hours | 24 hours | 48 hours |
| LOT A | | | | | | |
| Rabbit 1: | 19.8 | 10.1 | 25.0 | 21.7 | 11.8 | 21.0 |
| Rabbit 2: | 21.3 | 7.9 | 10.8 | 14.3 | 11.6 | 31.0 |
| Rabbit 3: | 19.7 | 11.0 | 21.9 | 22.3 | 29.8 | 22.2 |
| Mean ± SD: | 20.2 ± .7 | 9.7 ± 1.6 | 19.2 ± 7.5 | 19.4 ± 4.5 | 17.7 ± 10.5 | 24.7 ± 5.5 |
| VISCOAT™ | | | | | | |
| Rabbit 1: | 15.5 | 9.1 | 41.1 | 31.1 | 10.7 | 24.0 |
| Rabbit 2: | 23.1 | 36.8 | 9.6 | 8.5 | 8.4 | 31.1 |
| Rabbit 3: | 11.9 | 8.1 | 40.1 | 14.6 | 14.0 | 24.3 |
| Mean ± SD: | 16.8 ± 5.7 | 18.0 ± 16.3 | 30.3 ± 18.0 | 18.1 ± 11.7 | 11.0 ± 2.8 | 26.5 ± 4.0 |

TABLE III

| | Intraocular Pressure/mm Hg | | | | | |
|---|---|---|---|---|---|---|
| | Pre-Injection | 1 hour | 3 hours | 5 hours | 24 hours | 48 hours |
| LOT A' | | | | | | |
| Rabbit 1: | 32.9 | 9.4 | 12.1 | 13.8 | 19.2 | 3.4 |
| Rabbit 2: | 20.7 | 20.6 | 38.5 | 34.8 | 33.5 | 30.7 |
| Rabbit 3: | 23.3 | 30.3 | 32.8 | 26.5 | 37.8 | 19.4 |
| Mean ± SD: | 25.6 ± 6.4 | 20.1 ± 10.5 | 27.8 ± 18.9 | 25.0 ± 10.6 | 30.2 ± 9.7 | 28.0 ± 7.7 |
| HEALON™ | | | | | | |
| Rabbit 1: | 16.0 | 7.9 | 6.1 | 7.8 | 20.1 | 10.8 |
| Rabbit 2: | 15.3 | 13.7 | 16.2 | 26.0 | 34.5 | 16.3 |
| Rabbit 3: | 19.0 | 6.4 | 15.3 | 25.2 | 15.5 | 18.6 |
| Mean ± SD: | 16.7 ± 2 | 9.3 ± 3.9 | 12.5 ± 5.6 | 19.7 ± 10.3 | 23.4 ± 9.9 | 15.2 ± 4.0 |

The data of TABLES II and III demonstrate that collagen viscoelastic solutions according to the present invention, LOT A, are equal to or superior to prior art solutions LOT A' (collagen solution according to U.S. Pat. Nos. 4,713,446 and 4,851,513), Healon™ (sodium hyaluronate), or Viscoat™ (a mixture of sodium hyaluronate and chondroitin sulfate) when left in the anterior chamber of the eye. Viscoelastic solutions according to the present invention are easier to irrigate out of the intraocular cavities. They are anticipated to be substantially removed from the eye following ocular surgery and, thus, result in still fewer incidents of elevated intraocular pressure relative to prior art solutions.

In view of the present specification and appended claims, various additions, modifications, and omissions will be obvious to those skilled in the art and are within the invention as claimed below.

We claim:

1. A viscoelastic solution comprising an acylated soluble collagen and a mucopolysaccharide in a saline physiologic diluent having an ionic strength of no more than 0.001μ, said collagen and mucopolysaccharide being in a weight ratio of collagen to mucopolysaccharide of between about 100:1 and about 20:1, and said solution having a kinetic viscosity ranging from 1,000 cps to 800,000 cps, said solution having an osmolarity of between about 260 to 340 milliosmoles, with about 75 to about 95% of the osmolarity of said solution provided by nonionic solutes.

2. The viscoelastic solution according to claim 1 wherein said mucopolysaccharide is selected from the group consisting of chondroitin sulfate A, chondroitin sulfate B, chondroitin sulfate C, salts of hyaluronic acid, keratan sulfate, heparin sulfate and mixtures thereof.

3. The viscoelastic solution according to claim 1 wherein said nonionic solute is selected from the group consisting of glycerol, sorbitol, xylitol, threitol, mannitol, arabitol, ribitol, adonitol, erythritol, dulcitol, altritol, iditol, heptose, hexoses, pentoses and mixtures thereof.

4. The viscoelastic solution of claim 3 wherein said nonionic solute is glycerol.

5. The viscoelastic solution according to claim 1 wherein the kinetic viscosity ranges from 45,000 cps to 80,000 cps.

6. The viscoelastic solution according to claim 1 further comprising a growth factor in a concentration ranging from 10 ng/ml to 10,000 ng/ml.

7. The viscoelastic solution according to claim 6 wherein the growth factor is selected from the group consisting of growth hormone, interleukins, epidermal growth factors, fibroblast growth factors, insulin-like growth factors and mixtures thereof.

8. A collagen-based viscoelastic solution comprising acylated soluble collagen and a growth factor dissolved in a saline physiologic diluent, said growth factor having a concentration ranging from 10 ng/ml to 10,000 ng/ml, and said diluent having an ionic strength of no more than 0.001μ and said solution having an osmolarity ranging from 200 m osmol to 400 m osmol, wherein about 75 to about 95% of the osmolarity of said solution is provided by nonionic solutes.

9. A method of treating a patient comprising injection of a viscoelastic composition comprising an acylated soluble collagen in a saline physiologic buffer to separate and protect tissues being treated, said saline physiologic buffer having an ionic strength of no more than 0.001μ and said solution having an osmolarity ranging from 200 m osmol to 400 m osmol, wherein about 75 to about 95% of the osmolarity of said solution is provided by nonionic solutes.

10. The method of claim 9 wherein said nonionic solute is selected from the group consisting of glycerol, sorbitol, xylitol, threitol, mannitol, arabitol, ribitol, adonitol, erythritol, dulcitol, altritol, iditol, heptose, hexoses, pentoses and mixtures thereof.

11. The method of claim 10 wherein said nonionic solute is glycerol.

12. The method of claim 9 wherein the kinetic viscosity of said viscoelastic composition is between about 1,000 cps and 800,000 cps.

13. The method of claim 12 wherein the kinetic viscosity of said viscoelastic composition is between about 45,000 cps and 85,000 cps.

14. The method of claim 9 wherein the kinetic viscosity of said viscoelastic composition drops at least 88% upon the addition of salt to increase the ionic strength to at least 0.0022μ.

15. The method of claim 9 wherein said viscoelastic composition further comprises a mucopolysaccharide and wherein the weight ratio of said collagen to said mucopolysaccharide ranges between about 100:1 and about 20:1.

16. The method of claim 15 wherein said mucopolysaccharide is chondroitin sulfate.

17. The method of claim 9 wherein said viscoelastic composition further comprises between about 10 ng/ml and about 10,000 ng/ml of a growth factor.

18. A method of inserting an intraocular lens into the posterior or anterior chamber of a human or animal eye comprising:

introducing into said anterior or posterior chamber an effective amount of a viscoelastic solution comprising acylated soluble collagen and a saline physiologic diluent having an ionic strength of no more than 0.001μ and said solution having an osmolarity ranging from 200 m osmol to 400 m osmol, wherein about 75 to about 95% of the osmolarity Of said solution is provided by nonionic solutes, said amount sufficient to reduce the trauma which normally results from inserting an intraocular lens into said chamber in the absence of a viscoelastic solution, and inserting said lens into said chamber.

19. The method of claim 18 further comprising a physiologic saline irrigation step following said insertion, said irrigation sufficient to remove substantially all of said viscoelastic solution.

20. A process of preparing a viscoelastic solution consisting essentially of reconstituting acylated soluble collagen in a saline physiologic diluent having an ionic strength of no more than 0.001μ, said solution having an osmolarity ranging from 200 m osmol to 400 m osmol, wherein about 75 to about 95% of the osmolarity of said solution is provided by nonionic solutes.

21. A viscoelastic solution consisting essentially of acylated soluble collagen and a mucopolysaccharide in a saline physiologic diluent having an ionic strength of no more than 0.001μ and said solution having an osmolarity ranging from 200 m osmol to 400 m osmol, and a kinetic viscosity from 45,000 cps to 80,000 cps wherein bout 75 to about 95% of the osmolarity of said solution is provided by nonionic solutes.

22. A viscoelastic solution consisting essentially of acylated soluble collagen in a saline physiologic diluent having an ionic strength of no more than 0.001μ and said solution having an osmolarity ranging from 200 m osmol to 400 m osmol, and a kinetic viscosity ranging from 45,000 cps to 80,000 cps, wherein bout 75 to about 95% of the osmolarity of aid solution is provided by nonionic solutes.

23. A method of treating a patient with visco-surgery comprising injection of a viscoelastic composition of soluble collagen in a saline physiologic buffer to separate and protect tissues being treated, said saline physiologic buffer having an ionic strength of no more than 0.001μ and said solution having an osmolarity ranging from 200 m osmol to 400 m osmol, wherein about 75 to about 95% of the osmolarity of said solution is provided by nonionic solutes.

* * * * *